United States Patent [19]

Richard

[11] 4,304,012

[45] Dec. 8, 1981

[54] INTRAOCULAR LENS ASSEMBLY WITH IMPROVED MOUNTING TO THE IRIS

[75] Inventor: David A. Richard, San Dimas, Calif.

[73] Assignee: Iolab Corporation, San Dimas, Calif.

[21] Appl. No.: 82,047

[22] Filed: Oct. 5, 1979

[51] Int. Cl.³ .......................... A61F 1/16; A61F 1/24
[52] U.S. Cl. ....................................................... 3/13
[58] Field of Search ......................................... 3/13, 1

[56] References Cited

U.S. PATENT DOCUMENTS

| | | | |
|---|---|---|---|
| 4,073,015 | 2/1978 | Peyman et al. | 3/13 |
| 4,159,546 | 7/1979 | Shearing | 3/13 |
| 4,174,543 | 11/1979 | Kelman | 3/13 |
| 4,192,022 | 3/1980 | La Haye | 3/13 |
| 4,206,518 | 6/1980 | Jardon et al. | 3/13 |

FOREIGN PATENT DOCUMENTS 2556665  6/1977  Fed. Rep. of Germany ........... 3/13

*Primary Examiner*—Ronald L. Frinks
*Attorney, Agent, or Firm*—Donal B. Tobin

[57] ABSTRACT

An artificial intraocular lens assembly adapted for placement within the anterior or posterior chamber of the eye and for permanent attachment to the iris through natural ingrowth of living tissue, is disclosed. The lens assembly comprises a light refracting lens body and at least one lens support member which includes a portion having a surface contoured for intimate contact with the iris. A plurality of apertures are provided in the portion of the lens support member. After initial surgical affixation of the lens assembly within the eye, tissue of the iris grows into and through the apertures thereby anchoring the lens assembly within the eye.

7 Claims, 9 Drawing Figures

U.S. Patent      Dec. 8, 1981      4,304,012
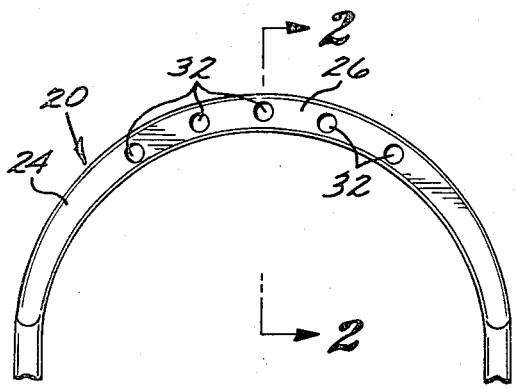
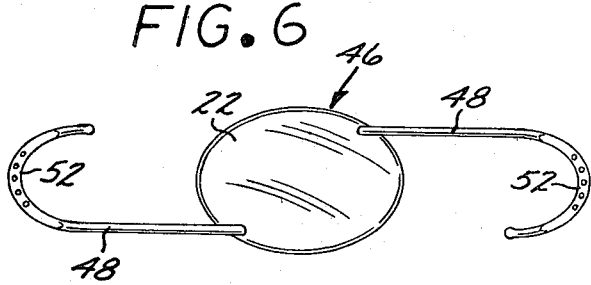
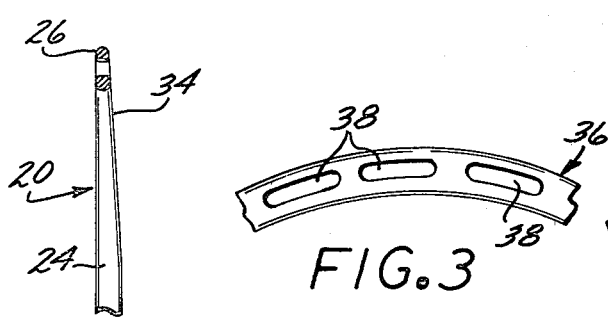
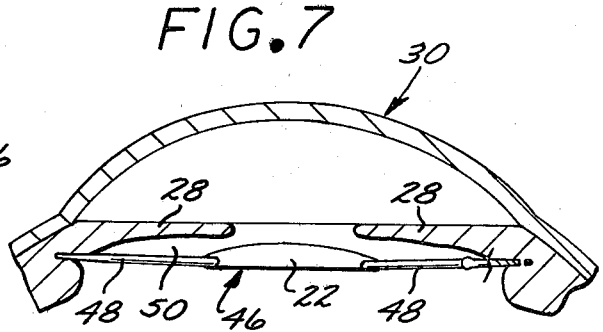
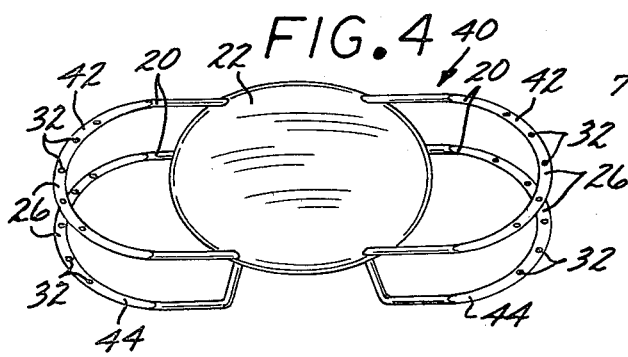
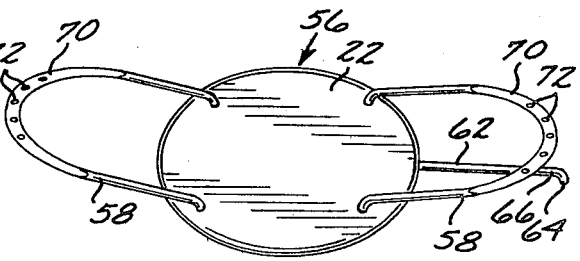
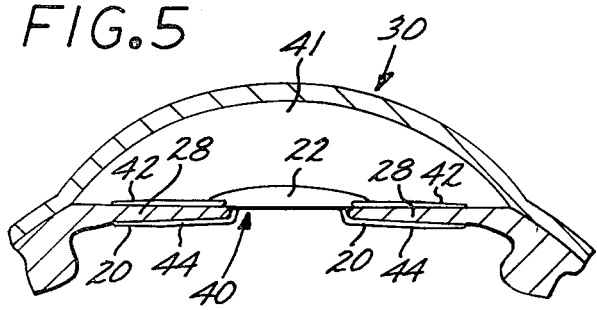
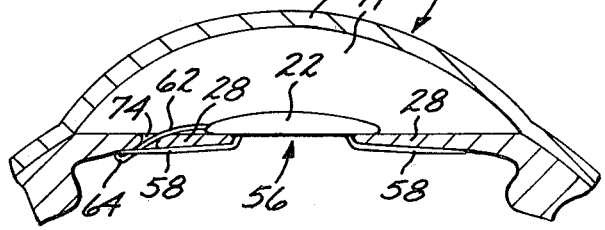

INTRAOCULAR LENS ASSEMBLY WITH IMPROVED MOUNTING TO THE IRIS

BACKGROUND OF THE INVENTION

1. Field of the Invention

The present invention relates to an intraocular lens assembly, and more particularly to an improved posterior chamber intraocular lens assembly which, after surgical affixation within the eye, is further anchored in the eye by natural ingrowth of a tissue of the iris of the eye.

2. Description of the Prior Art

The prior art is well aware of artificial intraocular lens assemblies which are surgically introduced into the human eye to replace the natural lens of the eye. One of the common reasons for removing the natural lens of a patient is a condition of lenticular disease known as a cataract. The prior art has developed a large variety of lens assemblies for surgical implantation either in the anterior chamber or attached to the iris of the eye.

Generally speaking, anterior chamber lenses of the prior art are placed between the iris and the cornea, and rely upon a precise size measurement to wedge the lens into a permanent position. The implantation of some of the artificial intraocular lens assemblies requires surgical incision or suturing to the iris. Other lens assemblies are kept in an operative position within the eye by a plurality of loops which embrace the iris and therefore "clip" the lens assembly to the iris. A recent posterior chamber lens, the SHEARING lens, is held in a relatively fixed operative position by spring like properties of a number of strands composed of plastic material, see U.S. Pat. No. 4,159,546.

For further detailed description of specific intraocular lens assemblies, reference is made to the following U.S. Pat. Nos. 3,925,825; 3,922,728; 3,971,073; 3,673,616; 3,913,148; 3,906,551; 3,994,027; 3,866,249; 3,986,214 and 3,991,426.

Although the implantation of artificial intraocular lens assemblies have become accepted by the medical profession, the artificial intraocular lens assemblies of the prior art can suffer from certain disadvantages such as dislodgment from their initial operative position as a result of post operative movement of the patient's eye.

It is readily appreciated by those skilled in the art, that in order to obtain optimal results a compromise must be found between the relative strength of affixation of the lens to the eye which could become a source of undue irritation, or tissue errosion and the necessity to keep the lens in an operative position within the eye.

U.S. Pat. No. 4,073,015 describes an intraocular lens mounting system wherein a plurality of loops extend substantially laterally from a light refracting lens body. Fibrous material is attached to the outer edges of the loops in areas where the edges come into contact with the iris. The loops affix the lens to the iris, and the subsequent ingrowth of the tissue of the iris further anchors the loops to the iris. U.S. Pat. No. 3,458,870 describes a corneal lens implant wherein a holding member for the optical lens is surgically implanted into the cornea. The holding member has a plurality of holes into which the ingrowth of the corneal stroma is purported to occur to further anchor the corneal implant to the cornea.

The improved artificial lens assembly mountings of the present invention which may be utilized in anterior chamber as well as in posterior chamber lens assemblies represent a further significant advancement.

SUMMARY OF THE INVENTION

It is an object of the present invention to provide an intraocular lens assembly which, after initial surgical affixation into the eye, is further anchored by natural ingrowth of tissue into the lens assembly.

It is another object of the present invention to provide an improved intraocular lens assembly which is adapted for mounting an intraocular lens in either the posterior or the anterior chamber of the eye wherein it is permanently anchored by natural ingrowth of the tissue.

It is still another object of the present invention to provide a posterior chamber artificial intraocular lens assembly which is free of sharp edges and surfaces capable of irritating the eye tissue, while being anchored by natural ingrowth of iris tissue.

It is yet another object of the present invention to provide an artificial intraocular lens assembly which is anchored to the iris by the natural ingrowth of tissue and which is relatively economical to manufacture.

These and other objects and advantages are attained by an artificial intraocular lens assembly having a light refracting lens body and at least one lens haptic support member mounted to the lens body. The lens support member can be adapted for mounting to the lens either in the anterior or posterior chamber of the eye and has at least one surface contoured for disposition in intimate contact with the iris or other eye tissue. The surface is provided with a plurality of apertures which penetrate through the lens support member. After initial surgical implantation into the eye, natural ingrowth of the tissue occurs into and through the apertures thereby further anchoring the lens assembly in operative position within the eye.

The objects and features of the present invention are set forth in the appended claims. The present invention may be best understood by reference to the following description, taken in connection with the accompanying drawings in which like numerals indicate like parts.

BRIEF DESCRIPTION OF THE DRAWINGS

FIG. 1 is a partial plan view of a first preferred embodiment of an improved mounting loop of a first artificial intraocular lens assembly designed in accordance with the present invention;

FIG. 2 is a partial cross sectional view of the first preferred embodiment of the improved mounting loop of the first artificial intraocular lens assembly, the cross section being taken at lines 2,2 of FIG. 1;

FIG. 3 is a partial plan view of a second preferred embodiment of an improved mounting loop of the present invention;

FIG. 4 is a top perspective view of the first artificial intraocular lens assembly incorporating the first preferred embodiment of the improved mounting loop of the present invention;

FIG. 5 is a schematic, cross sectional view of a human eye incorporating the first artificial intraocular lens assembly;

FIG. 6 is a top perspective view of an improved posterior artificial intraocular lens assembly designed in accordance with the present invention;

FIG. 7 is a schematic cross sectional view of the human eye incorporating the posterior chamber intraocular lens assembly;

FIG. 8 is a bottom perspective view of a third artificial intraocular lens assembly designed in accordance with the present invention, and FIG. 9 is a schematic cross sectional view of the human eye incorporating the third artificial intraocular lens assembly.

DESCRIPTION OF THE PREFERRED EMBODIMENTS

The following specification taken in conjunction with the drawings sets forth the preferred embodiments of the present invention in such a manner that any person skilled in ophthalmology lens design and ophthalmological surgery can use the invention. The embodiments of the invention disclosed herein are the best modes contemplated by the inventor for carrying out his invention in a commercial environment, although it should be understood that various modifications can be accomplished within the parameters of the present invention.

Referring now to FIGS. 1 and 2, a first preferred embodiment of an improved haptic mounting loop 20 of an artificial intraocular lens assembly is disclosed. The mounting loop 20 is similar in many respects in design and construction to several mounting loops of artificial intraocular lens assemblies of the prior art. It is mounted to a light refracting lens body 22, such as shown on FIG. 4, according to standard practice in the ophthalomogical lens art. An important novel feature of the first preferred embodiment of the mounting loop 20 of the present invention is, however, that the mounting loop 20 comprises a thin flexible filament or member 24 having at least one substantially flat surface 26 which is contoured and positioned for intimate juxtaposition to the iris 28 of the eye 30. In contrast, mounting loops or strands of prior art intraocular lens assemblies usually comprise a filament of substantially circular cross section.

As is shown on the plan view of FIG. 1, a plurality of holes or pores 32 are provided on the substantially flat surface 26 of the mounting loop 20. The holes or apertures 32 thus provide a porous surface in intimate contact with the iris 28. Experience has shown that a natural ingrowth of the tissue of the iris 28 occurs into the holes or apertures and anchors the mounting loop 20 to the iris 28. Although, for the sake of better illustration only 5 holes or apertures 32 are shown on FIG. 1, best results are obtained when the surface 26 in intimate contact with the iris 28 contains approximately 10 to 12 holes or apertures 23 available for tissue ingrowth. Good results are obtained when the holes or apertures 32 are circular, as is shown in FIGS. 1 and 2. The diameter of the circular apertures is in the range of 0.002 to 0.006 inches with a perference for a diameter of approximately 0.004 inch.

In the first preferred embodiment of the mounting loop 20 of the present invention, the 0.004 inch diameter of the circular apertures 32 comprises approximately 60% of the width of the filament 24. The material from which the filament 24 of the loop 20 may be made of, does not appear to be critical for the purpose of the present invention. Nevertheless, as is well established in intraocular lens design, the materials of an intraocular lens assembly must be carefully chosen for strength and biocompatibility. According to standard practice, mounting loops, staves and strands may be made from polypropylene or perhaps less desirably from a platinum—iridium alloy of a known composition. The light refracting lens body 22 is usually made from polymethylmethacrylate. For the purpose of practicing the present invention, the mounting loop 20 is preferrably manufactured from polypropylene, although other, otherwise acceptable materials, may also be used such as nylon.

A convenient method of providing the holes or apertures 32 in the polypropylene body of the filament 24 of the loop 20 is to punch the holes with a suitable die. In addition, the holes or apertures 32 may be incorporated in the filament 24 when the filament 24 itself is molded. As another alternative, the holes 32 may be provided by puncturing the the body of the filament 24 with laser beams.

As is best shown in the cross sectional view of FIG. 2, the holes or apertures 32 penetrate through the entire body of the filament 24. This is important for the purposes of the present invention because experience has shown that the tissue of the iris 28 actually grows through the aperture 32 and develops an enlarged rivet head like protrusion (not shown) on the lower side 34 of the filament body 24. As a result, the mounting loop 20 becomes very steadily anchored to the iris 28.

The partial plan view of FIG. 3 shows a second preferred embodiment of a haptic mounting loop 36 which, instead of circular holes or apertures, is provided with a plurality of oval shaped holes or apertures 38. A major axis or length of the oval apertures exceeds approximately 2 to 4 times the diameter of the circular holes or apertures 32 described for the first preferred embodiment of the mounting loop 20. A minor axis or width of the oval apertures 38 is however in the same 0.002 to 0.006 inch range. Very good results are obtained when the minor axis or width of the oval apertures 38 is approximately 0.004 inches.

Referring now specifically to FIGS. 4 and 5, a first intraocular lens assembly 40 is disclosed which incorporates four mounting loops 20 in accordance with the first preferred embodiment of the mounting loops 20 of the present invention. The first intraocular lens assembly is substantially of the type described in U.S. Pat. No. 3,906,551, the specification of which is hereby expressly incorporated by reference. In accordance with the present invention, however, each mounting loop 20 contains a substantially flat surface 26 contoured and positioned for intimate contact with the iris 28 after the intraocular lens assembly 40 is implanted within the anterior chamber 41 of the human eye 30. Briefly, the first intraocular lens assembly 40 has a pair of upper loops 42, and a pair of lower loops 44. When the lens assembly 40 is surgically mounted within the eye 30, as is shown on FIG. 5, the iris 28 is positioned between the respective upper and lower loops 42 and 44 and may be secured by sutures. Since the loops 42 and 44 are provided with the circular apertures 32 for accommodating an ingrowth of tissue, in due course of time the tissue of the iris 28 literally grows through the apertures 32 anchoring the intraocular lens assembly 40 to the iris 28.

It should be readily appreciated by those skilled in the art that the above described affixation of the intraocular lens assembly 40 within the eye 30 through natural ingrowth of tissue represents a significant advancement over prior art modes of attachment. The "riveting" effect of the live tissue of the iris 28 which grows through the apertures 32 results in an even stronger attachment of the lens assembly 40 to the iris 28 than the attachment obtained by ingrowth of tissue into fibrous material, as is described in U.S. Pat. No. 4,073,015. An artificial intraocular lens assembly attached within the eye in accordance with the present invention will resist accidental dislocation, and shows good biocompatibility with the eye tissue.

Referring to FIGS. 6 and 7, a posterior chamber artificial intraocular lens assembly 46 which incorporates a pair of mounting strands 48 designed in accordance with the present invention, is disclosed as a preferred embodiment of the present invention. The second artificial intraocular lens assembly 46 is generally of the type described in U.S. Pat. No. 4,159,546. The specification of this patent is hereby expressly incorporated by reference.

Briefly, the second artificial lens assembly 46 is adapted for mounting a lightweight refracting lens body 22 within the posterior chamber 50 of the eye 30. The lens assembly 46 includes a pair of haptic mounting strands 48 which extent substantially laterally from the light refracting lens body 22 with a curved free standing end. The mounting strands 48 are manufactured from a biocompatible elastic material which lends spring like properties to the mounting strands 48. Polypropylene is very well suited for this purpose. Each of the mounting strands 48 of the second artificial lens assembly 46 incorporates, in accordance with the present invention, a surface 52 which is contoured for disposition in intimate contact with the base 54 of the iris 28 when the artificial lens assembly 46 is properly inserted within the eye 30. The surface 52 includes at least a plurality of apertures 54 adjacent the outer extremity of the lens support that are available for ingrowth of the tissue of the iris 28. The number and dimensions of the apertures 54 are substantially the same as is described above for the first preferred embodiment of the mounting loop 20 of the present invention.

As is shown on FIG. 7, the second artificial lens assembly 46 is surgically inserted in the posterior chamber 50 of the eye 30 so that the elastic mounting strands 48 resiliently support the light refracting lens body 22 behind the pupil and within the optical axis of the eye. It is desirable to insure that the initial surgical anchored position is to be maintained since the lens must be capable of functioning for a number of years. After the initial surgical placement of the lens assembly 46 has taken place, ingrowth of tissue of the iris 28 into the apertures 54 in the resilient haptic support further strongly anchores the artificial lens assembly 46 within the eye 30. Thus a lightweight lens assembly is provided that will not be substantially affected by sudden inertia movements of the patients eye while still permitting the lens body 22 to be resiliently supported to facilitate both the initial implanting, e.g. the strands can collapse to enter through the pupil and subsequent centering of the optical lens body.

Referring to FIGS. 8 and 9, a third artificial lens assembly 56 which incorporates a third specific embodiment of the novel mounting loops 58 of the present invention, is disclosed. The third artificial lens assembly 56 is adapted for mounting a light refracting lens body 22 in the anterior chamber 41 of the eye 30. A pair of the mounting loops 58 are mounted below the light refracting lens body 22 in such a manner that the mounting loops 58 project away from the lens body 22 in an angular configuration. Stated in another way, geometrical planes respectively defined by each of the mounting loops 58 meet the plane of the lens body 22 at a slight accute angle, as is shown on FIGS. 8 and 9. Both loops 58 are conveniently manufactured from surgical grade polypropylene. A mounting stave 62 also made from surgical grade polypropylene, projects laterally outwardly from the light refracting lens body 22. A small protrusion 64 is provided at a remote end 66 of the stave 62 so that the protrusion projects upwardly towards the cornea 68 of the eye 30. The protrusion 64 provides a continuous camming surface so that the stave 62 may be smoothly passed through the mounting loop 58 and upon release hooks the entire lens assembly 56 to the iris 58, as is shown on FIG. 9.

Each mounting loop 58, in accordance with the present invention, includes surfaces 70 contoured for disposition in intimate contact with the iris 28. Each of the surfaces 70 are provided with a plurality of circular apertures 72 which are available for natural ingrowth of the tissue of the iris 28. The number and dimensions of the apertures 72 are substantially identical with the dimensions and numbers of apertures 32 described for the first preferred embodiment of the mounting loop 20 of the present invention.

As it should be readily apparent from the above description and from an inspection of FIGS. 8 and 9, in order to mount the third artificial lens assembly 56 within the eye a surgical incision 74, shown on FIG. 9, is first made within the iris 28. Both loops 58 are simply inserted behind the iris and the stave 62 is led through the incision 74. The stave 62 is then bent sufficiently to engage a position below the mounting loop 58. When the stave 62 is released, the protrusion 64 at the remote end 66 of the stave 62 engages the mounting loop 58 so that the entire lens assembly 56 is fixedly attached to the iris 28. After this initial, surgical affixation the naturally occuring tissue ingrowth into the apertures 72 further anchors the lens assembly 56 to the eye 30.

It is to be emphasized that the description of the several specific embodiments of the present invention is intended to be examplary rather than limiting in nature. Accordingly, they may be readily modified without departing from the scope and spirit of the present invention. What is critical for the purpose of the present invention is that at least one mounting appendage of an intraocular lens assembly is provided with a surface contoured for intimate juxtaposition to the iris 58 without irritation and contains a plurality of acceptable apertures which penetrate through the entire body of the mounting appendage. An artificial intraocular lens assembly constructed in accordance with the present invention is first affixed within the anterior or posterior chamber of the eye in accordance with the prior art. Subsequent to the initial surgical affixation, tissue ingrowth into the apertures strongly attaches the artificial intraocular lens assembly to the iris without any undue irritation of the iris. Since the hereinbefore described specific embodiments of the present invention readily lend themselves for further modifications by those skilled in ophthalmological surgery and in the ophthalmological lens design arts, the scope of the present invention should be interpreted solely from the following claims.

What is claimed is:

1. An intraocular lens assembly adapted for implantation into a living eye, the lens assembly comprising:
   a light refracting lens body, and,
   a plurality of flexible strands extending substantially laterally from the lens body, each strand having a curved portion and forming a loop;
   the curved portion of said strand spaced furthest apart from said lens body including a flat portion, said flat portion including a number of pores therethrough and adapted for intimate contact with the supporting structure of the eye, the pores being adapted to receive an ingrowth of tissue of the supporting structure of the eye, whereby after a surgical implantation of the lens and the attachment of the lens assembly to the supporting structure of the eye, a further fixation of the lens assembly to the supporting structure of the eye occurs through ingrowth of tissue into the pores.

2. The lens of claim 1 wherein said curved strands each include a first end secured adjacent the peripheral edge of said lens body and the other end is unsecured to form an open loop and said strand extends generally in the plane of the lens body.

3. The lens of claim 1 wherein said flat portion of said curved strand is aligned generally in the plane of the lens body.

4. The invention of claim 1 wherein the plurality of curved strands comprise a first pair of loops adapted to be disposed in front of the iris in the anterior chamber of the eye and a second pair of loops adapted to be disposed behind the iris in the posterior chamber of the eye, the first and second pair of loops respectively having said flat portions with pores for intimate contact with the iris.

5. The invention of claim 1 wherein the lens body is adapted for disposition in front of the iris in the anterior chamber of the eye, said plurality of curved strands comprising a pair of loops and a stave, the loops are adapted to be disposed behind the iris, and one of the loops is secured by the stave, said flat portions adapted for intimate contact with the iris.

6. In a posterior chamber artificial intraocular lens assembly adapted for implantation in the posterior chamber of the human eye as a replacement for the natural lens of the eye, the lens assembly having a light refracting lens body and at least one thin, elastic, flexible haptic strand extending laterally from the lens body and adapted for fixation to the base of the iris of the eye, the improvement comprising:

at least a portion of said strand having a flattened surface contoured for disposition in intimate contact with the base of the iris, the flattened surface portion having a plurality of apertures placed therethrough at approximately the outer extremity of said strand for additionally anchoring said strand to the iris to facilitate a growth of tissue into and through the apertures.

7. The improvement of claim 6 wherein said apertures are generally oval shaped with the longer dimension of the oval extending generally axially along said strand.

* * * * *